United States Patent [19]

Pavlin

[11] Patent Number: 4,503,267

[45] Date of Patent: Mar. 5, 1985

[54] EXTRACTION OF PHENOLICS FROM HYDROCARBONS

[75] Inventor: Mark S. Pavlin, Lawrenceville, N.J.

[73] Assignee: Union Camp Corporation, Wayne, N.J.

[21] Appl. No.: 544,772

[22] Filed: Oct. 24, 1983

[51] Int. Cl.³ .................... C07C 37/86; C07C 37/70
[52] U.S. Cl. .................................. 568/753; 568/749; 568/756; 568/758
[58] Field of Search ................ 568/753, 756, 758, 749

[56] References Cited

U.S. PATENT DOCUMENTS

| | | | |
|---|---|---|---|
| 2,381,209 | 8/1945 | Cotton | 568/753 |
| 2,786,085 | 3/1957 | Bloch | 568/753 |
| 2,789,143 | 4/1957 | Arnold et al. | 568/756 |
| 2,806,886 | 9/1957 | Neuworth | 568/753 |

Primary Examiner—Werren B. Lone
Attorney, Agent, or Firm—Kane, Dalsimer, Kane, Sullivan and Kurucz

[57] ABSTRACT

Polyethylene glycols have been found to be selective solvents for the extraction of phenolic compounds from admixture with hydrocarbons.

5 Claims, No Drawings

EXTRACTION OF PHENOLICS FROM HYDROCARBONS

BACKGROUND OF THE INVENTION

1. Field of the Invention

The invention relates to the separation of phenolic compounds from admixture with hydrocarbon compounds and more particularly relates to the liquid-liquid extraction of phenolic compounds from admixture with non-aromatic hydrocarbons, into polyethylene glycols.

2. Brief Description of the Prior Art

Phenolic compounds are generally found in association with a wide variety of hydrocarbon compositions such as the heavy hydrocarbons derived from coal liquefaction processes, terpene products of the wood chemicals industry and like industrial processes. Many of these phenolic compounds are considered undesirable contaminants, because of their reactivity, corrosivity and/or toxicity.

A number of processes have been developed and used to separate phenolic compounds from hydrocarbons. A major process comprises extraction into water of the phenates, obtained by reaction of the phenolic with caustic. The disadvantage of this process resides in the simultaneous extraction of non-phenolics, making further purification of the reconstituted phenolics necessary if they are to be recovered.

The method of the present invention is an advantageous advance in the art, enabling one to separate even low concentrations of phenolic compounds from non-aromatic hydrocarbon compounds, in a single step. The separated phenolics may be recovered from the extracting glycols, when so desired.

Polyethylene glycol has been known previously to be a solvent for certain organic compounds; see for example U.S. Pat. No. 2,902,428.

SUMMARY OF THE INVENTION

The invention comprises a method of separating phenolic compounds from admixture with a non-aromatic hydrocarbon, which comprises; extracting the phenolic compounds from the admixture into a liquid polyethylene glycol.

The term "phenolic compounds" as used herein means phenol and structurally related compounds such as cresol, resorcinol, hydroquinone and the like.

DETAILED DESCRIPTION OF THE PREFERRED EMBODIMENTS OF THE INVENTION

The method of the invention may be employed to separate phenolic compounds from admixture with a wide variety of hydrocarbon compositions. Representative of such hydrocarbon compositions are the heavy hydrocarbon products of coal liquefaction processes, crude petroleum oils, petroleum oil distillates and the like. Particularly advantageous is the method of the invention applied to the separation of phenolics from terpene hydrocarbons such as dipentene and the like.

The method of the invention is carried out by simply contacting the hydrocarbon mixture, while in a liquid state, with the polyethylene glycol (also in a liquid state) sufficiently intimately so as to selectively extract the phenolic compounds into the polyethylene glycol. The phenolic compounds are highly soluble in the polyethylene glycols.

Representative of the polyethylene glycols which may be used in the method of the invention are those having molecular weights of from about 200 to about 1500.

The extraction of the phenolics may be carried out over a wide range of temperatures, i.e., on the order of from about 20° C. to about 200° C. Selection of an advantageous temperature may be dictated by the temperature required for liquefaction of the hydrocarbon and/or the polyethylene glycol.

The pressure under which the method of the invention is carried out is not critical and may be under sub- or super-atmospheric pressures, preferably under normal atmospheric pressures.

The proportion of polyethylene glycol employed in the method of the invention is one sufficient to extract the phenolic compounds from admixture with the hydrocarbon composition. In general, such a proportion will be in the range of from about 0.1 to 3.0 volumes of the polyethylene glycol for each volume of mixture to be extracted.

The procedure for the method of the invention may be carried out by conventional solvent extraction techniques. Batch mixing and settling may be employed or continuous and countercurrent operations may be employed. For example, it is particularly preferred to carry out the process by introducing the glycol at an upper portion of a treating tower to flow downwardly countercurrent to the mixture to be treated which is introduced near the bottom of the treating tower. Packing elements, perforated plates, or other contacting aids can be employed in such a system. A raffinate phase constituting the extracted mixture and minor portions of polyethylene glycol may be removed overhead from such a tower. An extract phase, principally constituting the polyglycol together with minor amounts of constituents removed from the extracted mixture can be removed from the bottom of the treating tower.

Solvent may be recovered from the raffinate and extract phases by conventional techniques. Thus, a simple distillation procedure permits removal of the polyglycols for recycle to the solvent system. Alternatively, solvent may be recovered by cooling the extract and raffinate phases substantially below the extraction temperature. Cooling in this manner results in a change in solvent properties sufficient to liberate the polyglycols for recycle to the extraction system.

Alternatively, solvent may be recovered by adding water to the extract and raffinate phases. The addition of water causes the separation of an upper oil layer and a lower layer comprising an aqueous solution of polyethylene solvent. The lower, aqueous solvent layer is withdrawn and may be dehydrated by distillation or other means for recycling to the extraction zone.

The following examples describe the manner and the process for carrying out the invention and set forth the best mode contemplated by the inventor for carrying out the invention but are not to be construed as limiting the scope of the invention.

EXAMPLE 1

An appropriate vessel was charged with 10.0 gms of alpha-pinene and 0.50 gms of o-cresol. To the charge there was added 7.0 gms of polyethylene glycol having a M.W. of 400 (Carbowax 400; Union Carbide Corp.). The resulting mixture was stirred for 2 hours at room temperature. Upon separation of the alpha-pinene, an aliquot was subjected to gas chromatography. The analysis is as follows, compared to an analysis of the starting material.

| Peak | Area % Starting Material | Alpha-pinene after Treatment |
|---|---|---|
| alpha-pinene | 91.48 | 95.62 |
| beta-pinene | 1.68 | 1.71 |
| Camphene | 2.06 | 2.09 |
| o-Cresol | 3.80 | 0.05 |

This procedure achieved about 98.7% depletion of the o-cresol.

EXAMPLE 2

In an appropriate vessel, 0.50 g p-methoxyphenol was dissolved in 25 g of warm 1-octene. To this solution was added 15 g of polyethylene glycol, 1000 M.W. (Carbowax 1000) solid. This mixture was stirred 2 h at 50° C. then cooled to 20° C. The polyethylene glycol solidified and the 1-octene was decanted. The recovered 1-octene (23.1 g) contained 160 ppm p-methoxyphenol. Removal efficiency was 99.2%.

EXAMPLE 3

In a 500 ml, 3-neck, round-bottom flask, equipped with an electric stirrer were placed 100 g mixed terpene hydrocarbons (dipentenes) containing 1000 ppm hydroquinone and 100 g of polyethylene glycol, 600 M.W. (Carbowax 600, Union Carbide, supra.). After the mixture was stirred for 3 h at room temperature, the layers were allowed to settle and a sample was taken from the top layer for gas chromatographic analysis. The treated dipentene contained about 10 ppm hydroquinone. Removal efficiency was about 99%.

What is claimed:

1. A method of separating phenolic compounds from admixture with a non-aromatic hydrocarbon, which comprises; extracting the phenolic compounds from the admixture into a liquid polyethylene glycol having a molecular weight of at least 200.

2. The method of claim 1 wherein the polyethylene glycol has a molecular weight of from 200 to 1500.

3. The method of claim 1 wherein the extract is then separated from the admixture.

4. The method of claim 1 wherein the polyethylene glycol is employed in a proportion of from 0.1 to 3.0 volumes for each volume of admixture.

5. A method of separating hydroquinone from a mixture of hydroquinone and mixed terpene hydrocarbons, which comprises; extracting the hydroquinone from the mixed hydrocarbons into a liquid polyethylene glycol having a molecular weight of at least 200.

* * * * *